US00PP25284P3

(12) United States Plant Patent
Bacon

(10) Patent No.: US PP25,284 P3
(45) Date of Patent: Feb. 10, 2015

(54) NECTARINE TREE NAMED 'SUNECTWENTYFOUR'

(50) Latin Name: ***Prunus persica* var. *nucipersica***
Varietal Denomination: Sunectwentyfour

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 184 days.

(21) Appl. No.: 13/694,270

(22) Filed: Nov. 14, 2012

(65) Prior Publication Data

US 2014/0137303 P1 May 15, 2014

(51) Int. Cl.
*A01H 5/00* (2006.01)

(52) U.S. Cl.
USPC ..... Plt./190

(58) Field of Classification Search
CPC ..... A01H 5/0856; A01H 5/0837
USPC ..... Plt./190
See application file for complete search history.

*Primary Examiner* — June Hwu

(74) *Attorney, Agent, or Firm* — Knobbe, Martens, Olson & Bear, LLP

(57) ABSTRACT

A new and distinct nectarine tree variety, *Prunus persica* var. *nucipersica* 'Sunectwentyfour' is characterized by early ripening, large sized fruit, lower chilling requirements and nearly 100% over-color.

1 Drawing Sheet

Latin name of the genus and species claimed: *Prunus persica* var. *nucipersica.*

Variety denomination: 'Sunectwentyfour'.

BACKGROUND AND SUMMARY OF THE INVENTION

This invention relates to the discovery and asexual propagation of a new and distinct variety of nectarine, *Prunus persica* var. *nucipersica* 'Sunectwentyfour'. The new variety was first hybridized in 2002 and selected in 2004 by Terry Bacon as breeder number: 'NE338'. The new variety was first evaluated by Terry A. Bacon near Wasco, Calif. in Kern County. The variety 'Sunectwentyfour' was originated by hybridization.

The new variety 'Sunectwentyfour' is characterized by early ripening, large sized fruit, low chilling requirements and nearly 100% over-color.

The seed parent is '94-018N' (unpatented), and the pollen parent is not known as the pollen came from a bulk pollen mix originating from several unpatented low chill nectarine selections. The parent varieties were first crossed in February 2002, the date of first sowing being February 2003 and the date of first flowering being January 2004. The new nectarine variety 'Sunectwentyfour' was first asexually propagated by Terry Bacon near Wasco, Kern County, Calif. in June 2004 by budding.

The new variety 'Sunectwentyfour' is distinguished from its seed parent, '94-018N' (unpatented), in that the new variety ripens about seven days earlier than the seed parent and the new variety has nearly 100% over-color, while 94-018N (unpatented) has 60-75% over-color. The fruit size of the new variety is also larger at 69 mm, compared to 94-018N (unpatented) with a diameter of 60 mm.

The new variety 'Sunectwentyfour' has a similar ripening time as 'May Glo' (U.S. Plant Pat. No. 5,245), but the fruit is larger in size, at about 69 mm versus 62 mm for 'May Glo'.

The new variety 'Sunectwentyfour' has similar ripening time as 'Zee Fire' (U.S. Plant Pat. No. 13,501) but the new variety has a lower chilling requirement of 200 CH, compared to 300 CH for 'Zee Fire'. The fruit of the new variety is also larger in size, about 69 mm versus 66 mm for 'Zee Fire'.

The new variety 'Sunectwentyfour' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new nectarine variety 'Sunectwentyfour' taken from a six year old tree. The illustration shows a branch with leaves; side, bottom and top views of the fruit; a sectional view of the fruit divided across its suture plane to show the flesh and stone; and a ventral and side views of the dried stones removed. The photographic illustration was taken shortly after being picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 6 year old 'Sunectwentyfour' plants on Nemared (unpatented) rootstock, grown in the vicinity of Wasco, Kern County, Calif., and is believed to apply to plants of the variety grown under similar conditions of soil and climate elsewhere.

TREE

General: (Measurements taken on 6 year old tree unless otherwise noted.).

*Size*.—Large. Normal for most nectarine varieties. Reaches a height of approximately 3 meters including normal pruning.

*Spread*.—Normal for most nectarine varieties. Approximately 15 feet with normal vase pruning.

*Vigor*.—Strong. Approximately 1.8 to 2 meters of growth in the first growing season.

*Growth*.—Upright to spreading.

*Productivity*.—Productive. Fruit set is usually two or more times the desired amount for marketable size fruit. Thinning is necessary.

*Form*.—Vase formed.

*Bearer*.—Regular.

*Fertility*.—Self-fertile.

*Canopy density*.—Dense. Pruning is necessary to maintain tree vase shape and allow light into canopy.

*Hardiness*.—Hardy in all fruit growing areas of California.

*Disease resistance/susceptibility*.—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above soil line.).

*Diameter*.—Approximately 25 cm.

*Texture*.—Medium shaggy.

*Trunk color*.—Outer bark is a combination of Light Greyed-Green 198D and 178A Dark Greyed-Red. Trunk color becomes darker with age.

Branches: (Measurements at approximately 90 cm above soil line.).

*Size*.—Diameter ranges from approximately 8-10 cm.

*Texture*.—Smooth on young wood, increasing roughness with tree age.

*Color*.—A combination of Dark Greyed-Orange 166A and Light Greyed-Green 198D.

*Lenticels*.—Present.

*Lenticels numbers*.—Numerous.

*Lenticels density*.—Approximately 3-5 per $cm^2$.

*Lenticels color*.—About Medium Greyed-Orange 164C.

*Lenticels size*.—Medium.

*Lenticels length*.—Approximately 6 mm.

*Lenticels width*.—Approximately 2 mm.

Flowering shoots: (Data taken in June at midpoint of current-season growth.).

*Size*.—Average diameter approximately 5 mm.

*Color*.—Topside: About Dark Greyed-Brown 199A to Dark Green 141B. Underside: About Dark Green 141B.

*Thickness*.—Medium.

*Internode length*.—Medium; approximately 2 cm. Midway on flowering shoot.

*Flowering shoot lenticels*.—None observed.

*Flowering shoot leaf buds*.—Shape: Obovate. Width: Approximately 2 mm. Length: Approximately 3 mm. Color: About Dark Greyed-Orange 165A.

*Flowering shoot flower buds*.—Shape: Obovate. Width: Approximately 2.5 mm. Length: Approximately 4 mm. Color: About Dark Greyed-Orange 165A. Number of buds per node: Usually 2.

*Presence of anthocyanin coloration*.—Present, dark red.

*Density of buds*.—Medium.

*Flower bud distribution*.—Generally isolated on one year old shoots.

*Ratio of wood (leaf) buds to flowering shoots*.—½ on short spurs.

FOLIAGE

Leaves:

*Size*.—Medium.

*Average length*.—Medium; approximately 162 mm.

*Average width*.—Medium; approximately 40 mm.

*Thickness*.—Medium.

*Color*.—Upper surface: About Dark Green 135B, lower surface: About 135C.

*Form*.—Lanceolate.

*Tip*.—Acuminate.

*Base*.—V-shaped.

*Margin*.—Crenate.

*Venation*.—Pinately veined.

*Vein color*.—About Light Green 139D.

*Red mid vein on lower side*.—Present.

*Surface texture*.—Smooth on both upper and lower surfaces.

*Leaf blade (ratio of length to width)*.—High; approximately 5/1 ratio.

*Shape in the cross section*.—Concave.

*Angle at apex*.—Small.

*Angle at base*.—Acute.

*Profile*.—Up folded.

*Leaf blade tip*.—Curved downwardly.

*Angle of tip*.—Acute.

*Undulation of margin*.—Slight.

*Timing of beginning of leaf bud burst*.—Early.

Petiole:

*Average length*.—Medium; approximately 6 mm.

*Average diameter*.—Approximately 0.7 mm.

*Color*.—About Dark Greyed-Red 180A when dry.

*Nectaries*.—Present.

*Shape of nectaries*.—Reuniform.

*Thickness*.—Medium, approximately 1 mm.

Stipules:

*Number/leaf bud*.—Approximately 2 when present.

*Typical length*.—Medium, approximately 8 mm.

*Color*.—About Medium Yellow-Green 151A.

*Persistence*.—Falls off.

Leaf glands:

*Form*.—Reniform.

*Average number*.—About 3-4.

*Position*.—On both leaf base and petiole, alternate.

*Average size*.—Medium; approximately 1 mm long.

*Color*.—About Dark Greyed-Red 180A when dry.

FLOWERS

General:

*Flower blooming period*.—First bloom: Approximately first week in February. Location of First bloom: Toward base of tree. Full bloom: Approximately first week in February. Location of Full bloom: Midway on tree.

*Time of bloom*.—Early.

*Duration of bloom*.—Medium; approximately 10 days.

*Type*.—Campanulate (non-showy).
*Time of beginning of flowering*.—Early.
*Diameter of fully opened flower*.—Medium, approximately 32 mm.
*Flower aroma*.—Very slight.
*Corolla* (*main color on inner side*).—About Dark Red-Purple 63A.

Peduncle:
*Length*.—Medium; approximately 3-4 mm.
*Diameter*.—Medium; approximately 2 mm.
*Color*.—About Medium Yellow-green 146B.
*Pubescence*.—Absent.

Petals:
*Number*.—5.
*Arrangement*.—Free.
*Length*.—Approximately 15 mm.
*Diameter*.—Approximately 10 mm.
*Shape*.—Broadly ovate.
*Width*.—Medium.
*Apex shape*.—Rounded.
*Base shape*.—Narrows at point of attachment.
*Color* (*inner and outer surfaces*).—About Dark Red-Purple 63A.
*Surface texture*.—Smooth.
*Margins*.—Smooth, undulating.
*Frequency of flowers with double petals*.—None.
*Size*.—Medium approximately 10 mm wide.
*Claw length*.—Medium.
*Margin waviness*.—Medium.
*Base angle*.—Narrow.
*Division of upper margin*.—Entire.
*Pubescence of inner surface*.—Absent.
*Pubescence of outer surface*.—Absent.

Sepals:
*Number*.—5.
*Length*.—Approximately 5 mm.
*Diameter*.—Approximately 4 mm.
*Shape*.—Ovate.
*Color*.—About Medium Red 54B.
*Surface texture*.—Smooth to slightly bumpy.
*Margins*.—Smooth.
*Positioning*.—Not touching petals or receptacle.
*Pubescence of inner surface*.—Absent.
*Pubescence of outer surface*.—Absent.
*Frequency of flowers with double sepals*.—None.

Stamens:
*Number*.—Many, approximately 42.
*Average length*.—Approximately 7 mm.
*Filament color*.—White. 155A.
*Anther color*.—About Dark Red 53B when drying.
*Flower pollen color*.—About Dark Yellow-Orange 17B.
*Position compared to petals*.—Slightly below.

Pistil:
*Number*.—One, occasionally up to 4.
*Average length*.—Approximately 17 mm.
*Ovary diameter*.—Approximately 1-1.5 mm.
*Pubescence*.—None.
*Stigma extension in comparison to anthers*.—Above.
*Frequency of supplementary pistils*.—Few.

Flower buds:
*Hardiness*.—Hardy.
*Size*.—Medium, approximately 4 mm long and 2.5 mm wide.
*Length*.—Medium.
*Shape*.—Obovate.
*Positioning*.—Free.
*Pubescence*.—Few.
*Color*.—About Dark Greyed-Orange 165A.

Receptacle:
*Depth*.—Medium.
*Pubescence of inner surface*.—Absent.
*Pubescence of outer surface*.—Absent.

Ovary:
*Pubescence*.—Absent.

Style:
*Pubescence* (*of base*).—Absent.

FRUIT

General: (At firm-ripe, on tree managed to obtain maximum size for commercial production near Wasco, Kern County, Calif. Description taken near Wasco, Kern County, Calif. on May 14, 2012).).
*Harvest*.—
*Date of first pick*.—Approximately May 10, 2012.
*Date of last pick*.—Approximately May 20, 2012.
Maturity when described: Firm.
Season ripening: Early.
Position of maximum diameter: Towards the middle.
Symmetry about the suture: Slightly asymmetric.
Size:
*Average size*.—Large.
*Length* (*stem end to apex*).—Approximately 70 mm.
*Diameter in line with suture plane*.—Approximately 69 mm.
*Diameter perpendicular to suture plane*.—Approximately 69 mm.
*Average weight*.—Approximately 168 gm.
Apex shape: Rounded.
Apex base: Rounded.
Mucron tip at pistil end: Absent.
Shape of pistil end (excluding mucron tip): Weakly depressed under conditions in Bakersfield, Calif.
Symmetry (viewed from pistil end): Slightly asymmetric.
Fruit stem cavity:
*Shape*.—Rounded.
*Depth*.—Medium, approximately 3 mm.
*Breath*.—Approximately 1 cm.
*Width*.—Medium.
Fruit stem:
*Length*.—Medium, Approximately 7 mm.
*Diameter*.—Approximately 2 mm.
*Color*.—About Medium Greyed-Orange 164B.
*Adherence to stone*.—Strong.
Fruit skin:
*Thickness*.—Medium.
*Adherence to flesh*.—Strong.
*Surface texture*.—Smooth.
*Pubescence*.—Absent.
*Bloom*.—None.
*Ground color*.—About Medium Yellow-Orange 20B.
*Overcolor*.—About Dark Red 44B to Dark Red 46A.
*Taste*.—None.
*Firmness*.—Firm.
*Reticulation*.—Absent.
*Roughness*.—Absent.
*Tenacity*.—Tenacious to flesh.
*Relative area of over color of skin*.—Very large.
*Pattern of over color of skin*.—Solid to slightly blotchy.
*Tendency to crack*.—Slight, in wet season.

Flesh:

*Ripens*.—Evenly.

*Texture*.—Melting.

*Fibers*.—Moderate.

*Flavor*.—Bland tart-sweet.

*Brix*.—Approximately 11°-12°.

*Juice*.—Moderate.

*Aroma*.—Slight.

*Color*.—About Medium Yellow 11B.

*Sweetness*.—Low-Medium.

*Anthocyanin color of flesh in central part of flesh*.—Absent or very weak.

*Anthocyanin color of flesh next to skin*.—Absent or very weak.

*Anthocyanin color of flesh around stone*.—Absent or very weak.

*Amygdalin*.—Wanting.

*Acidity*.—Medium.

*Eating quality*.—Fair.

*Carotenoid coloration of flesh*.—About Medium Yellow 11B.

*Stone/flesh ratio*.—About 1/28 by weight.

*Firmness*.—Firm.

Pit cavity size:

*Length*.—Approximately 30 mm.

*Diameter in line with suture plane*.—Approximately 25 mm.

*Diameter perpendicular to suture plane*.—Approximately 20 mm.

*Color*.—About Medium Yellow 11B.

Depth of stalk cavity: Medium.

Width of stalk cavity: Medium.

Fruit use: Fresh market.

Fruit shipping and keeping quality: Good for early-season variety. Quality remains good up to 5 weeks at 0° C.

Stone: (Measurements taken on dried stones.)

*Stone freeness*.—Clings over entire surface.

*Adherence to flesh*.—Present.

*Degree of adherence to flesh*.—Strong.

*Stone size*.—Size: Medium. Size compared to Fruit: Small. Length: Medium, approximately 30 mm. Diameter in line with suture plan): Approximately 25 mm. Diameter perpendicular to suture plane: Approximately 20 mm. Width of Stalk End: Medium; approximately 5 mm. Angle of Stalk end: Right angle. Hilum: Oval.

*Stone form*.—Viewed from stem end: Oval-flattened. Viewed from side: Oval. Viewed from ventral side: Oval-flattened.

*Stone shape*.—Lateral view: Oval. Base shape: Nearly straight. Apex shape: Pointed.

*Relief of surface*.—Predominately pits.

*Stone surface*.—Pitted throughout.

*Stone halves*.—Nearly symmetric.

*Stone ridges*.—Continuous.

*Stone outgrowing keel*.—Well developed.

*Stone tendency to split*.—Low.

*Anthocyanin coloration*.—Absent.

*Intensity of brown color*.—Light.

*Position of maximum diameter*.—Middle.

*Sides*.—Equal.

*Pits*.—Circular-to-elongated.

*Fibers*.—Retains short fibre-like threads along ridges.

*Ventrical edge*.—Medium.

*Dorsal edge*.—Full, deep grooves.

*Kernel*.—Shape: oval with rounded base and pointed apex. Average length: 15 mm. Average width: 11 mm. Average depth (perpendicular to suture): 5 mm. Color: About 165B when dried.

What is claimed is:

1. A new and distinct nectarine tree as herein described and illustrated.

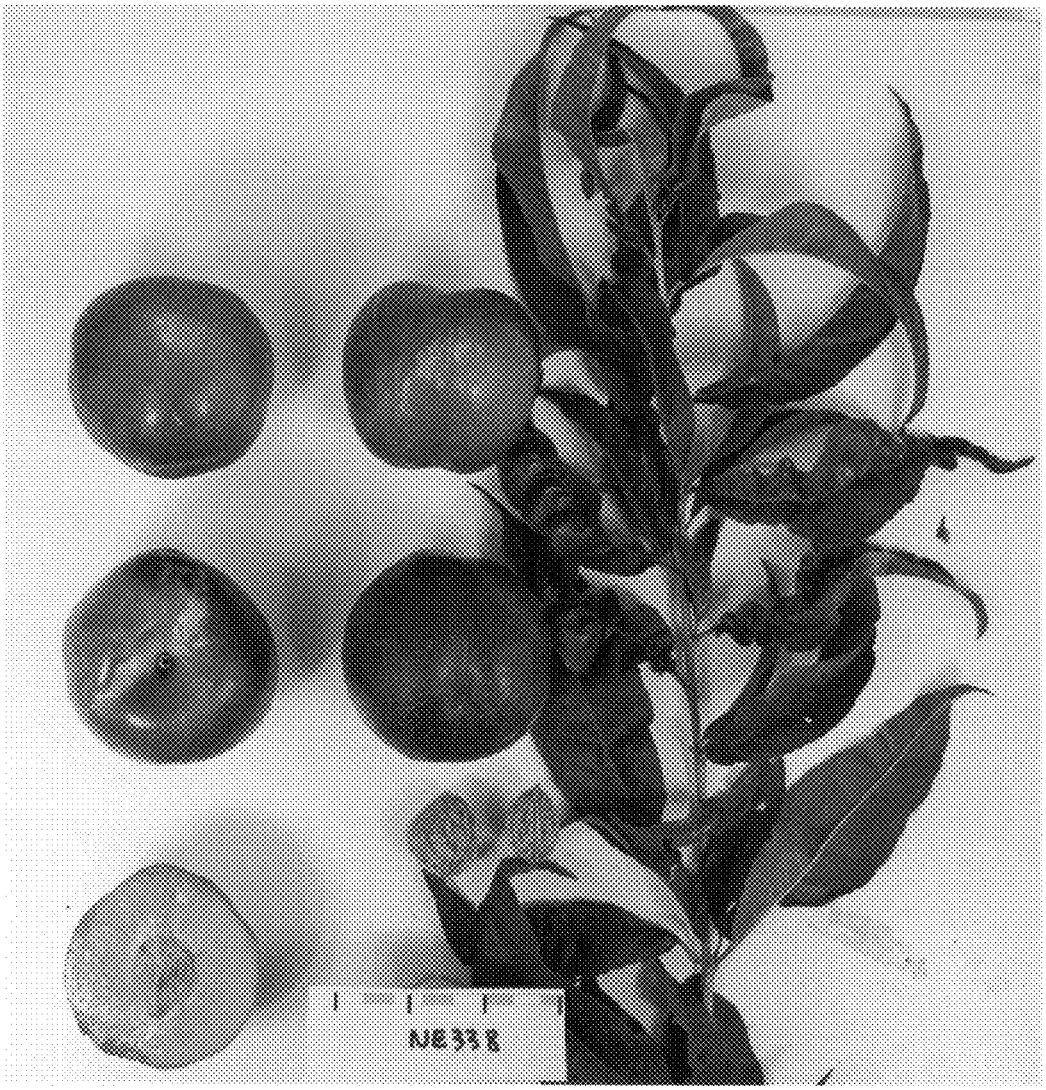

* * * * *